(12) United States Patent
Aiston et al.

(10) Patent No.: US 11,998,350 B2
(45) Date of Patent: Jun. 4, 2024

(54) FUNCTIONAL EEG MONTAGE FOR COGNITIVE SKILL DEVELOPMENT

(71) Applicant: Thynk, Inc., Windermere, FL (US)

(72) Inventors: Christopher James Aiston, Mont Vernon, NH (US); Wayne R. Boucher, Manchester, NH (US); Robert Andrew Charles, New Boston, NH (US); Brendan Patrick Collins, Manchester, NH (US); Daniel Goodwin, Derry, NH (US); Michael Thomas Herda, Boxford, MA (US); Adam Jacobs, Hollis, NH (US); Kee Sook Jeon, Warwick, RI (US); Daniel Patrick O'Sullivan, Mont Vernon, NH (US); James M. Sellers, Eliot, ME (US); John Richard Shambroom, Framingham, MA (US); Joseph St. Onge, Raymond, NH (US); Drew Sunstein, Exeter, NH (US)

(73) Assignee: Thynk, Inc., Windermere, FL (US)

( * ) Notice: Subject to any disclaimer, the term of this patent is extended or adjusted under 35 U.S.C. 154(b) by 603 days.

(21) Appl. No.: 15/579,736

(22) PCT Filed: Jun. 8, 2016

(86) PCT No.: PCT/US2016/036338
§ 371 (c)(1),
(2) Date: Dec. 5, 2017

(87) PCT Pub. No.: WO2016/200871
PCT Pub. Date: Dec. 15, 2016

(65) Prior Publication Data
US 2018/0279944 A1     Oct. 4, 2018

Related U.S. Application Data

(60) Provisional application No. 62/172,601, filed on Jun. 8, 2015.

(51) Int. Cl.
*A61B 5/00*     (2006.01)
*A61B 5/16*     (2006.01)
*G09B 19/00*     (2006.01)

(52) U.S. Cl.
CPC .............. *A61B 5/486* (2013.01); *A61B 5/168* (2013.01); *A61B 5/6803* (2013.01);
(Continued)

(58) Field of Classification Search
CPC ....... A61B 5/486; A61B 5/168; A61B 5/6803; A61B 5/0478; A61B 2562/0215; A61B 2560/0214; G09B 19/00
See application file for complete search history.

(56) References Cited

U.S. PATENT DOCUMENTS 5,038,782 A * 8/1991 Gevins ................ A61B 5/0017
600/383
5,800,351 A    9/1998 Mann
(Continued)

FOREIGN PATENT DOCUMENTS

CN    102596021 A    7/2012
CN    104665826 A    6/2015
(Continued)

OTHER PUBLICATIONS

Extended European Search Report for European Application No. 16808150.3, dated Oct. 9, 2018 (13 pages).
(Continued)

*Primary Examiner* — Christian Jang
(74) *Attorney, Agent, or Firm* — Clark & Elbing LLP

(57) ABSTRACT

The invention features a headset, and systems including the headset, equipped with electrical sensors. The headset is suitable for use by a child and suitable for use in a gaming system, e.g., to train attention.

20 Claims, 13 Drawing Sheets

(52) U.S. Cl.
CPC ............... *A61B 2560/0214* (2013.01); *A61B 2562/0215* (2017.08); *G09B 19/00* (2013.01)

(56) References Cited

U.S. PATENT DOCUMENTS

| | | | |
|---|---|---|---|
| 6,077,237 A | 6/2000 | Campbell et al. | |
| 8,473,024 B2 | 6/2013 | Causevic et al. | |
| 9,031,631 B2 | 5/2015 | Tong et al. | |
| 2002/0113427 A1* | 8/2002 | Nada | B42F 9/00 281/45 |
| 2006/0210377 A1* | 9/2006 | Rondeau | B42C 9/0018 412/1 |
| 2007/0249952 A1* | 10/2007 | Rubin | A61B 5/6814 600/544 |
| 2010/0041962 A1* | 2/2010 | Causevic | A61B 5/0478 600/301 |
| 2011/0015503 A1* | 1/2011 | Joffe | A61B 5/30 600/383 |
| 2012/0071781 A1* | 3/2012 | Fadem | A61B 5/6843 600/544 |
| 2012/0083673 A1 | 4/2012 | Al-Ali et al. | |
| 2012/0296569 A1* | 11/2012 | Shahaf | A61B 5/4064 702/19 |
| 2014/0257073 A1 | 9/2014 | Machon et al. | |
| 2014/0336449 A1 | 11/2014 | Wackym et al. | |

FOREIGN PATENT DOCUMENTS

| | | |
|---|---|---|
| EP | 2698099 A1 | 2/2014 |
| JP | 2014-036862 A | 2/2014 |
| JP | 2015-093137 A | 5/2015 |
| WO | WO-2008/109699 A2 | 9/2008 |
| WO | WO-2013/155280 A1 | 10/2013 |

OTHER PUBLICATIONS

International Search Report and Written Opinion for International Application No. PCT/US16/36338, dated Sep. 6, 2016 (15 pages).
Kim et al., "Implementation of portable multi-channel EEG and head motion signal acquisition system," Computing and Networking Technology (ICCNT), 2012 8th International Conference on, IEEE, Aug. 27, 2012, pp. 370-375.
TechCrunch: "Muse Brain Sensing Headband," Youtube, Sep. 22, 2014, <https://www.youtube.com/watch?v=Ern-WHr4rfl>, (1 page).

* cited by examiner

FUNCTIONAL EEG MONTAGE FOR COGNITIVE SKILL DEVELOPMENT

BACKGROUND OF THE INVENTION

The invention features a headset with electrical signal sensors suitable for use by children and adults and suitable for use in a gaming system, e.g., to train attention.

Electroencephalography (EEG) is the recording of electrical activity along the scalp. It measures voltage fluctuations resulting from the flow of current between neurons of the brain. Commonly, an EEG instrument is a clinical, multichannel device used to measure and display the brain waves of a user. The user's brain waves are monitored by the use of a number of electrodes placed in contact with the scalp in a predetermined pattern, such as the 10-20 system (also known as the international 10-20 system). Intermediate locations were added to create the 10-10 system (Guideline for Standard Electrode Position Nomenclature, American Clinical Neurophysiology Society, 2006). This placement system is an internationally recognized method for the placement of electrodes on the scalp of a user was developed to ensure standardized reproducibility so that a user's studies could be compared over time, and users could be compared to each other.

EEG measurements can be used to develop a 'cognitive signature' that can be used in a "smart" video game that responds to the child's precise cognitive levels of attention or inattention. The child controls the speed of a character in the game purely by using their ability to focus without touching a keyboard. Then in real-time, the game creates a fantasy world in which the child advances through a number of increasingly difficult tasks using the child's actual attention levels to develop attention and impulsivity control skills. The product then enables the child to transfer those newly learned skills into the real world, where they improve their academic performance and are better able to perform daily activities at home.

An electrode system to capture bioelectric signals, such as electroencephalograph (EEG) signals, from a user generally should address various requirements including safety needs, cost, power consumption, performance, ease of use, and user comfort. In a non-clinical application the relative importance of these factors may be somewhat different to that in a clinical application. For example, in a clinical application the electrodes are applied by a relatively skilled technician, whereas in non-clinical application the electrodes are more likely to be applied by a person with no training or knowledge of correct application or placement of the electrodes. Convenience and user comfort are also generally more important in a non-clinical application. A patient in a clinical situation is more likely to be tolerant of some level of discomfort or inconvenience when testing and calibrating electrodes than a person in a non-clinical setting. For example, a conventional clinical apparatus for applying electrodes to a user's head includes a flexible cap that covers the user's entire scalp and includes a strap beneath the chin, so that the cap may be snugly secured to the user's head. This type of apparatus can include over 100 electrodes for some clinical applications.

An electrode system for use by a child should be designed to (i) intuitively and conveniently place electrode sensors at predetermined anatomical positions on the head of the child without significant training, (ii) account for the variability in head size among children of different ages, and (iii) be comfortable to wear.

SUMMARY OF THE INVENTION

The invention features a headset that includes: (i) a front portion including a first end, a second end, a sensing bar, and a locator bar, wherein the sensing bar and the locator bar joined at the first end and the second end of the front portion and including a space below the sensing bar and above the locator bar between the first end and the second end, wherein (a) the sensing bar is shaped and configured to contact the forehead of a user wearing the headset and includes a first electrical sensor positioned to contact the forehead of the user at about position AF3 of the 10-10 system, the first electrical sensor including one or more electrodes, and a second electrical sensor positioned to contact the forehead of the user at about position AF4 of the 10-10 system, the second electrical sensor including one or more electrodes, and (b) the locator bar is shaped and configured rest upon the brow of the user; and (ii) a first side portion and a second side portion, the first side portion joined to the first end of the front portion and the second side portion joined to the second end of the front portion, wherein the first side portion, the second side portion, and the front portion, together, are shaped and configured to grip the head of the user. In particular embodiments, at least one of the first side portion and the second side portion further include a protrusion, the protrusion including a third electrode positioned to contact the user at about position M2 or M1 the third electrical sensor including one or more electrodes that contact the skin over the mastoid process of the user. The headset, or a system utilizing the headset, can further include a processor equipped with an electronics for selecting and detecting a difference in voltage between (i) AF3 and AF4, and (ii) AF4 and M2 or AF3 and M1. In particular embodiments, the headset further includes a ground electrode. The ground electrode can, for example, be positioned on the sensing bar between the first electrode sensor and the second electrode sensor.

The first side portion and the second side portion can be shaped and positioned to contact the skin over the temporal bone of the user. For example, the headset can be shaped to permit the user to wear the headset and eyeglasses (or ear buds) simultaneously. In particular embodiments, each of the first side portion and the second side portion further include padding positioned to contact the head of the user.

In particular embodiments, the space is a void having an approximately oval or geometric shape (e.g., approximately rectangular or approximately trapezoidal). The maximum distance between the inside edge of the locator bar and the inside edge of the sensing bar can be about 18 mm (e.g., 15±2 mm, 18±2 mm, or 20±2 mm). The maximum distance between the outside of the locator bar and the outside of the sensing bar can be about 42 mm (e.g., 40±2 mm, 42±2 mm, or 44±2 mm).

In certain embodiments, at least one of the first electrode, the second electrode, and the third electrode include a dry electrode, a fabric electrode, a silver electrode, or a silver fabric electrode. In some embodiments, at least one of the first electrode, the second electrode, and the third electrode is ½ inch or greater in at least one dimension. Each of the first electrode, the second electrode, and the third electrode can further include padding positioned to contact the skin of the user.

In particular embodiments, the sensing bar includes sockets for directly securing the first electrode and the second electrode and a ground electrode, or for receiving a mounting element into which the first electrode and the second electrode and a ground electrode are secured. The mounting element can use replaceable modules to permit control over the spacing between the first electrode and the second electrode. For example, the first electrode and the second electrode can be spaced 7±1 cm apart from center to center, or for larger heads the first electrode and the second electrode can be spaced from 8 cm to 10 cm apart from center to center.

The headset can include a battery and electronics for receiving, processing, and transmitting EEG signals collected from the user. For example, the first side portion can include a first housing, the second side portion can include a second housing, and the first housing and the second housing can include the battery and/or the electronics. The headset can be configured to wirelessly transmit the EEG signals to a host computer.

In one embodiment of the headsets of the invention, (i) the first side portion is slidably coupled to the first end of the front portion are and (ii) the second side portion is slidably coupled to the second end of the front portion to permit extension of the front portion and the side portions.

In another embodiment of the headsets of the invention, (i) the first side portion is rotatably coupled to the first end of the front portion are and (ii) the second side portion is rotatably coupled to the second end of the front portion to permit the side portions to fold inward and reduce the size of the headset when not in use.

In yet another embodiment of the headsets of the invention, the mastoid protrusion is coupled to the first side portion or the second side portion by a hinge. The hinge can be configured to permit the protrusion to fold toward the head of the user. In some embodiments, the hinge is a spring-loaded hinge configured to press the projection against the head of the user.

Optionally, the headset further includes a strap that connects the first side portion to the second side portion (i.e., securing the headset with a strap wrapping around the back of the head).

Optionally, the headset further includes an accelerometer.

In a related aspect, the invention features a system including: (i) a headset of the invention; and (ii) a processor equipped with an algorithm for analyzing the EEG signals to determine the attention level of the subject, wherein the headset and the processor are in wireless communication.

In still another aspect, the invention features a method of monitoring the attention level of a subject using a headset of the invention or a system of the invention.

As used herein, the term "AF3" refers to the AF3 position in the internationally recognized 10-20 system of placing EEG electrodes on the scalp, as extended to the 10-10 system. AF3 is located intermediate between Fp and F3 on the left side of the user's forehead.

As used herein, the term "AF4" refers to the AF4 position in the internationally recognized 10-20 system of placing EEG electrodes on the scalp, as extended to the 10-10 system. AF4 is located intermediate between Fp and F4 on the right side of the user's forehead.

As used herein, the term "AFz" refers to the AFz position in the internationally recognized 10-20 system of placing EEG electrodes on the scalp, as extended to the 10-10 system. AFz is located centrally between F3 and F4 on the middle of the user's forehead. The AFz electrode functions as a ground electrode. Alternatively, the ground electrode is positioned elsewhere in the headset.

As used herein, the term "M1" refers to the left mastoid position.

As used herein, the term "M2" refers to the right mastoid position.

As used herein, the term "electrical sensor" refers to a sensor used for measuring bioelectric signals, such as EEG or EMG signals. The electrical sensor can include one or more electrodes, optionally formed from a flexible conductive fabric.

As used herein, the term "front portion" refers to elements in the headsets of the invention position over the forehead of a user wearing the headset. The front portion includes two bars that stretch across the forehead, an upper sensing bar and a lower locator bar. The locator bar rests above the brow of the user. The sensing bar contacts the forehead and makes contact with, for example, the AF3 and AF4 and, optionally, AFz positions of the users forehead.

As used herein, the term "side portion" refers to that portion of the headset that grips on the head of the user. The side portions can be configured to contact any portion of each side of a users head. Desirably, the side portions contact the user over the scalp covering the temporal bone (i.e., sitting above, and not upon, the ears). The side portions are connected to each end of the front portion and, optionally, a head strap. The side portion can include one or two protrusions containing electrodes positioned to contact the skin above the mastoid process of the user (i.e., at position M1 or M2).

Other features and advantages of the invention will be apparent from the following Detailed Description, the drawings, and the claims.

DETAILED DESCRIPTION

The invention features an electrode system in the form of a headset designed for use by children and adults. The headsets of the invention are designed to (i) intuitively and conveniently place electrical sensors at positions AF3 and AF4 on the forehead of a child (i.e., without significant training in how to wear the headset), (ii) account for the variability in head size among children of different ages, and (iii) be comfortable to wear. For example, particular embodiments of the headsets of the invention are sized and configured to accommodate a range of head sizes from the $5^{th}$ percentile of 8 year old girls to the $95^{th}$ percentile of 18 year old boys. While the headset of the invention is designed for kids ages 8-18, it will also fit most adults as well, since the head size of an 18 year old boy is close to adult sized head.

Figure 1:
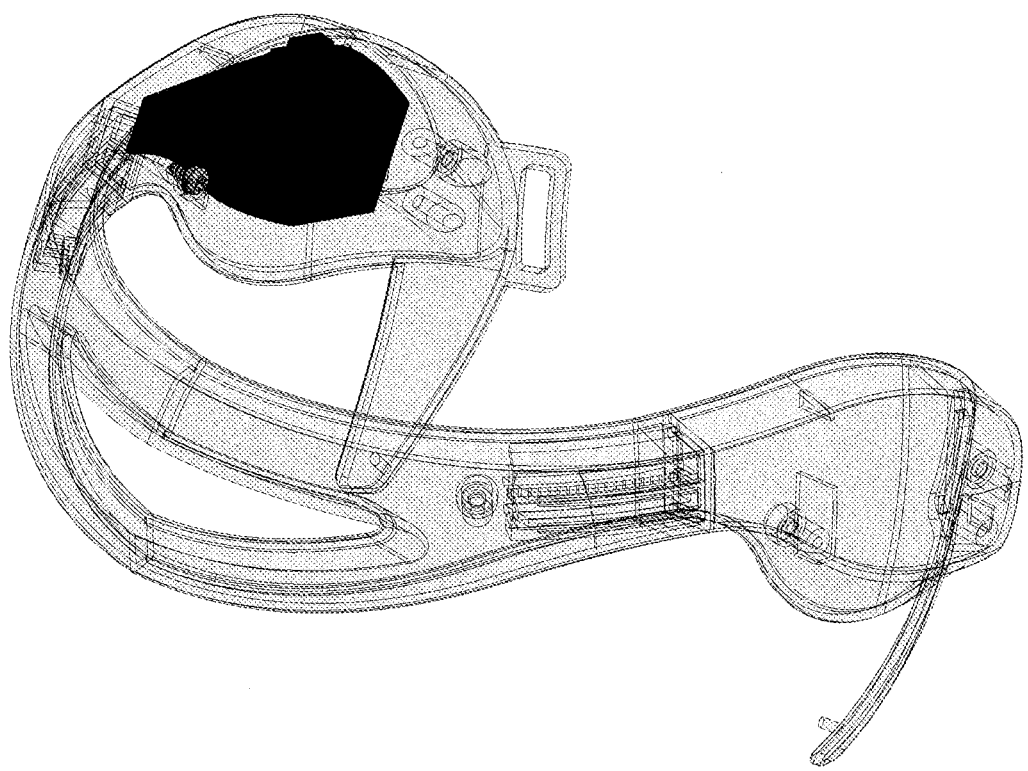
FIG. 1 is a drawing depicting a front perspective view of an embodiment of the headset of the invention. The dark shading on the left side portion corresponds to the battery and other electronics.
Figure 2:
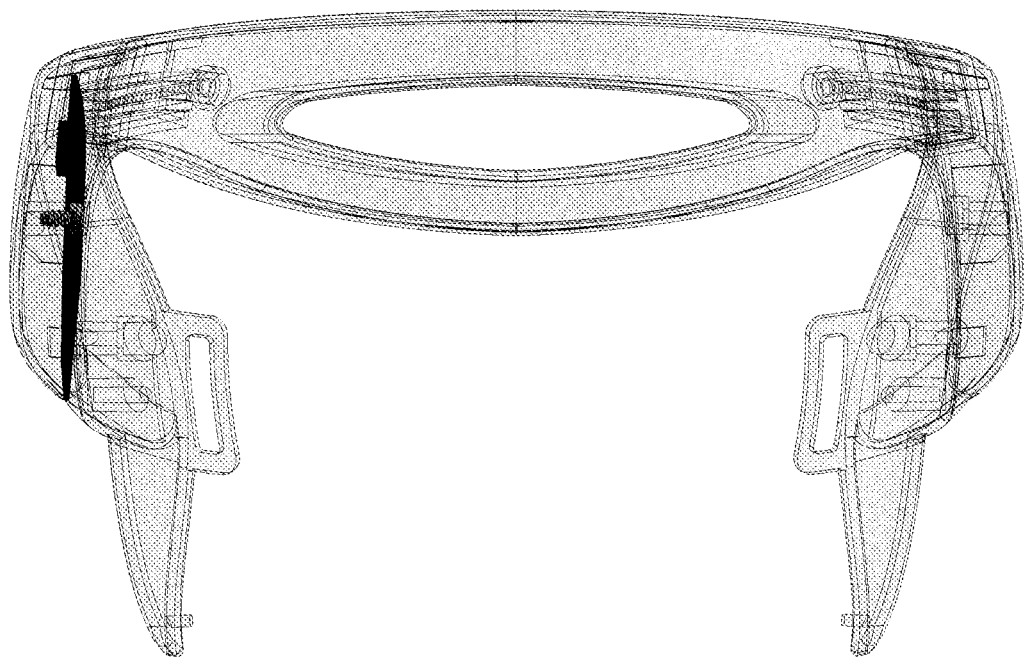
FIG. 2 is a drawing of the front view of an embodiment of the headset of the invention.
Figure 3:
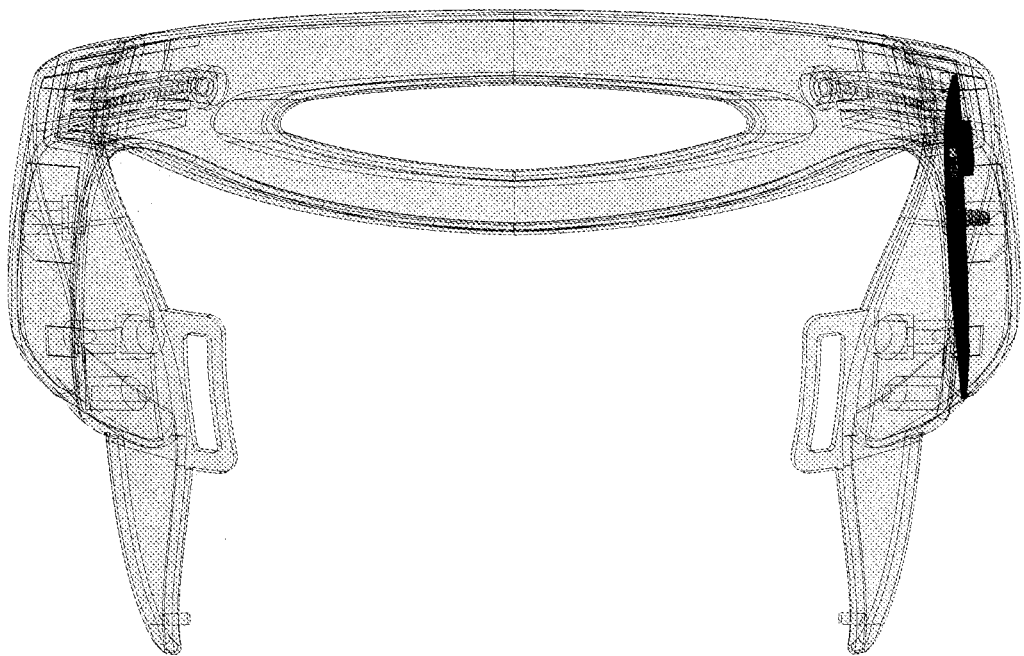
FIG. 3 is a drawing depicting a top view of an embodiment of the headset of the invention.
Figure 4:
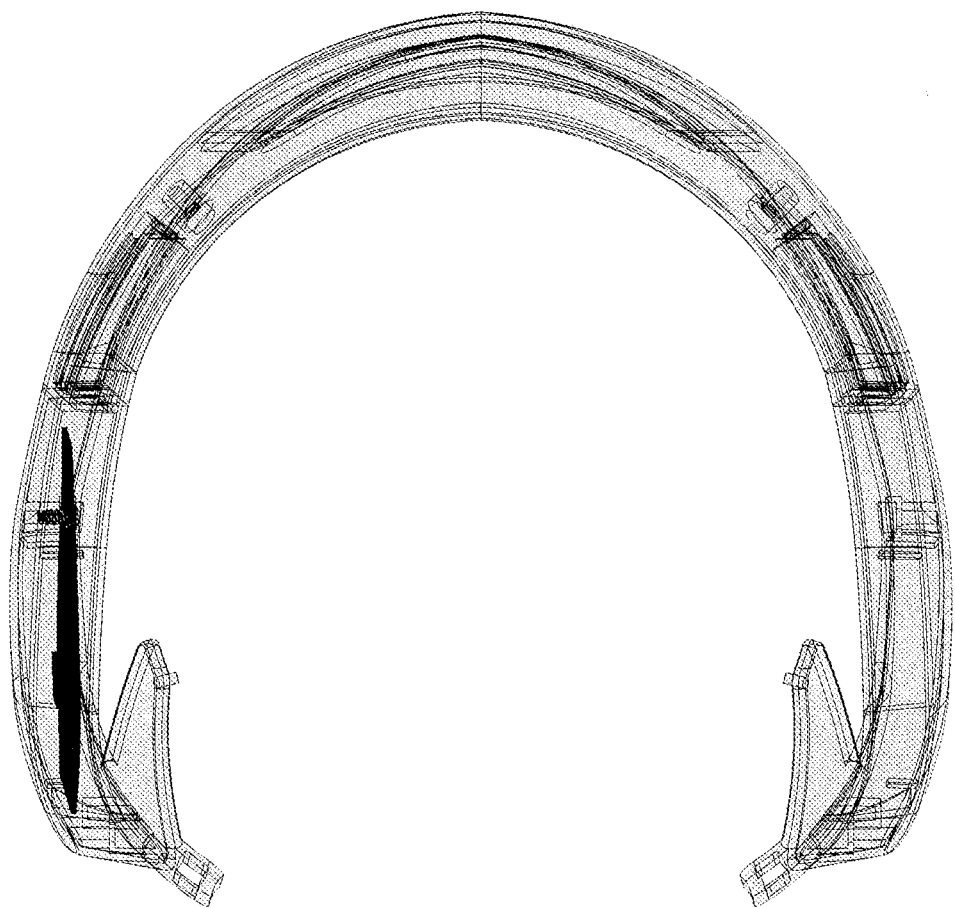
FIG. 4 is a drawing depicting a top view of an embodiment of the headset of the invention.
Figure 5:
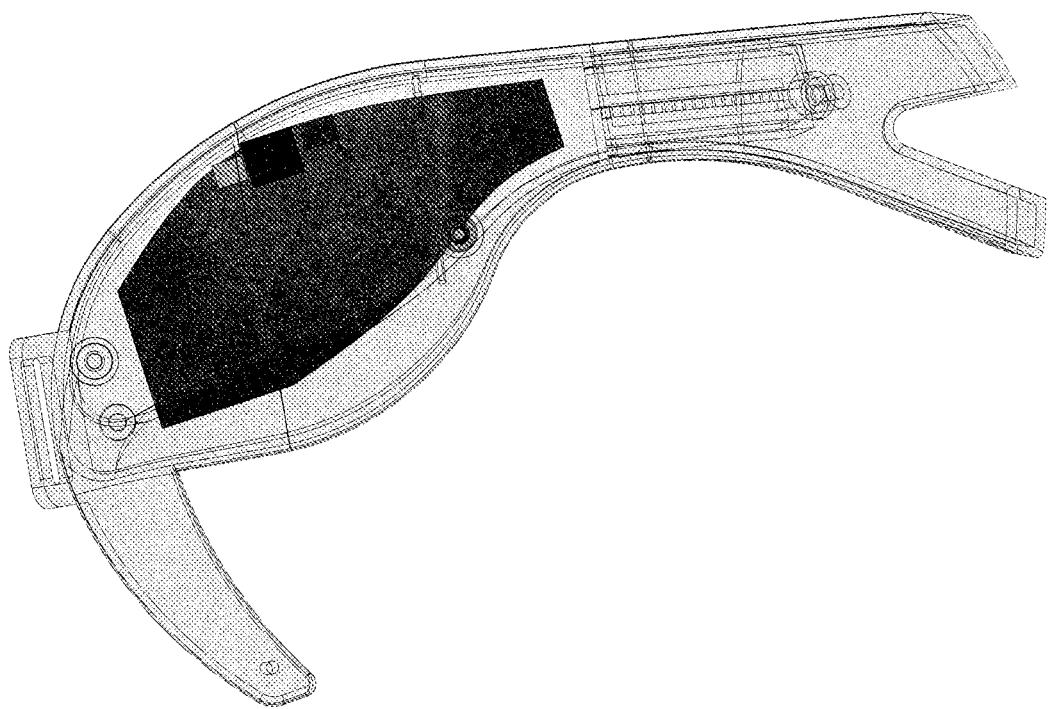
FIG. 5 is a drawing depicting the right side view of an embodiment of the headset of the invention. This drawing depicts the protrusion from the side portion that contacts the mastoid process.
Figure 6:
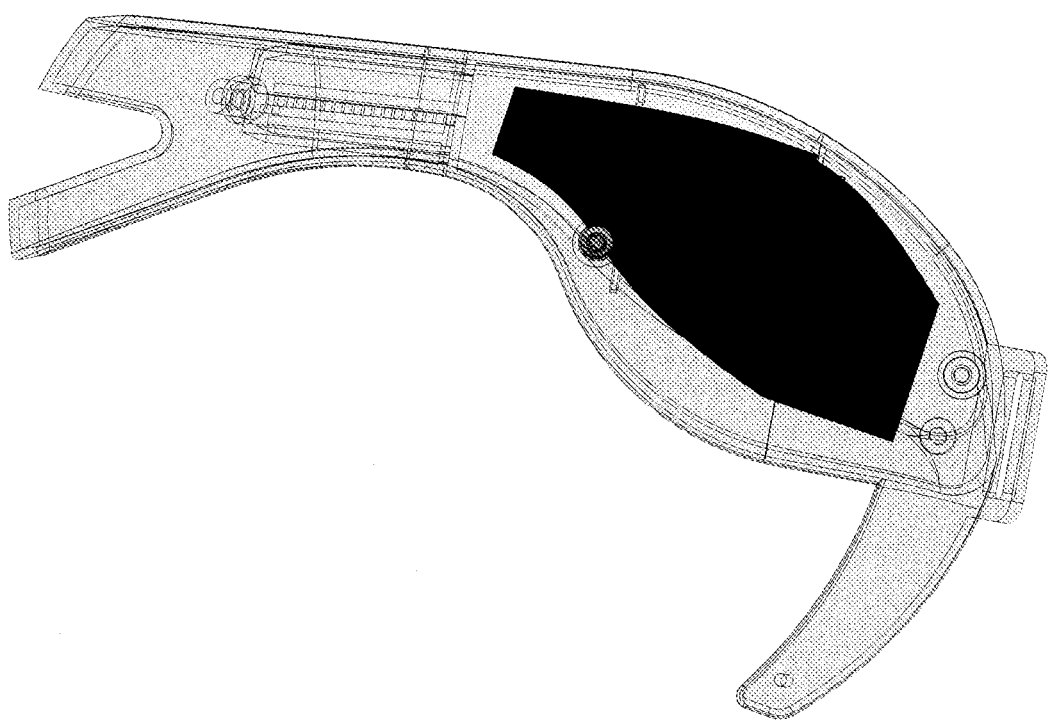
FIG. 6 is a drawing depicting the left side view of an embodiment of the headset of the invention.
Figure 7:
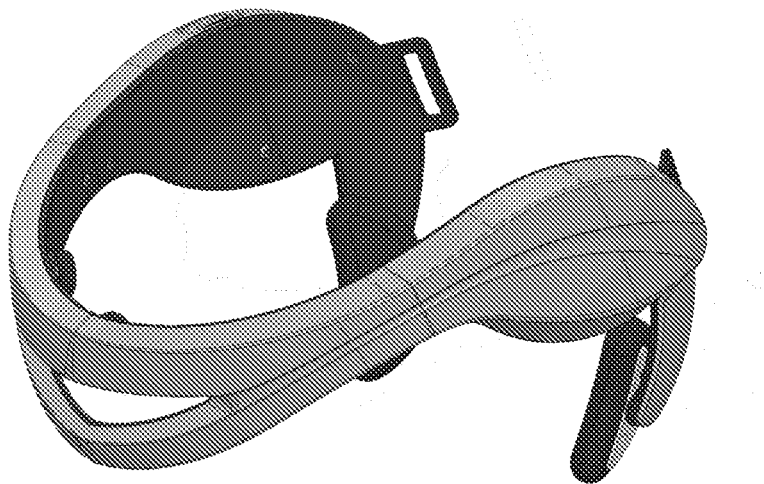
FIG. 7 is a picture of a perspective view of an embodiment of the headset. The headset has smooth lines and rounded contours. A slot for an electrode is visible on the sensing bar of the front portion.
Figure 8:
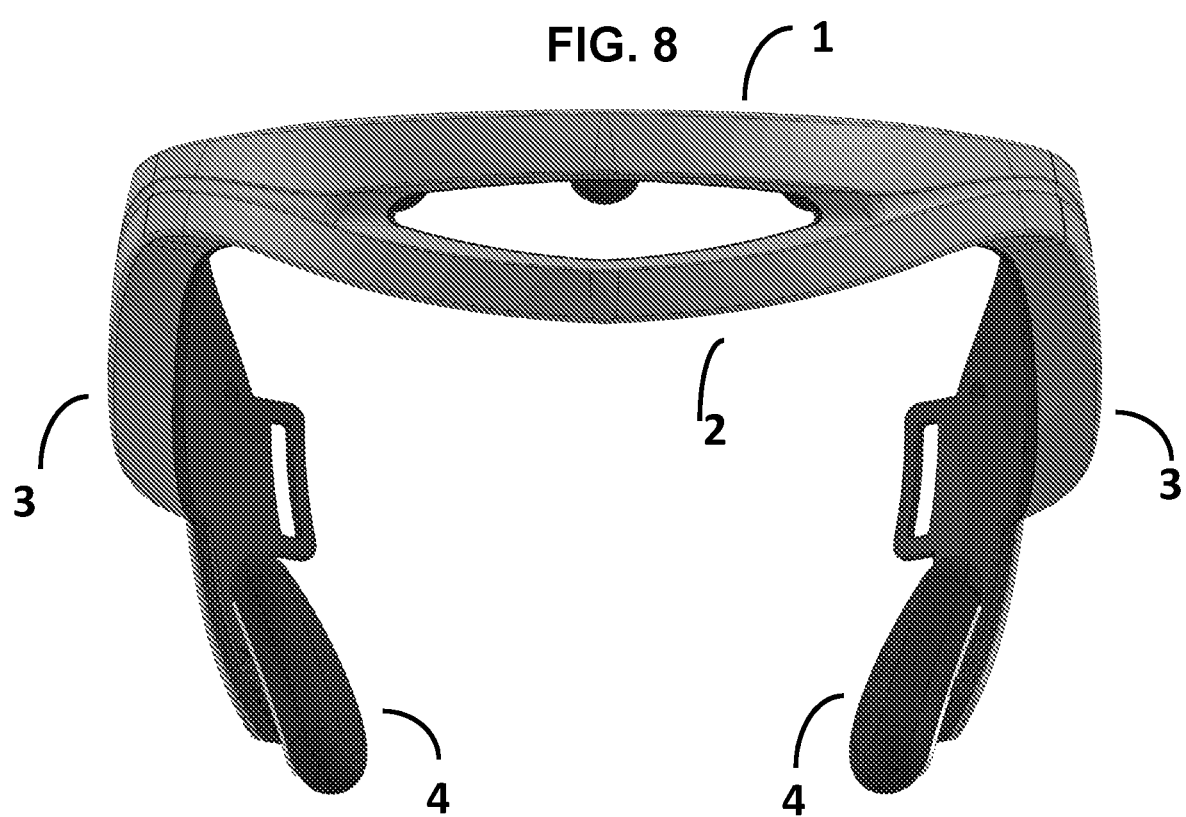
FIG. 8 is a picture of the front view of an embodiment of the headset, including a front portion having a sensing bar (1), a locator bar (2), first and second side portions (3), and protrusions positioned to contact a user at position M2 or M1 (4).
Figure 9:
FIG. 9 is a picture of the rear view of an embodiment of the headset. Visible in the front portion are rectangular recesses for the placement of the electrical sensors.
Figure 10A:
FIGS. 10A-10F depict different views of a subject wearing a headset of the invention.
Figure 10B:
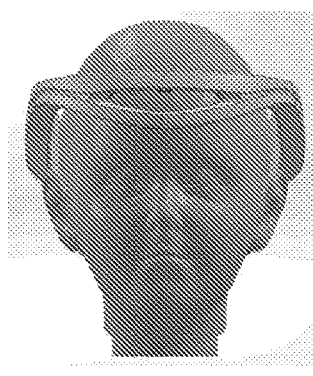
Figure 10C:
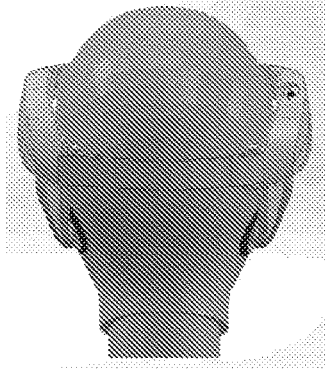
Figure 10D:
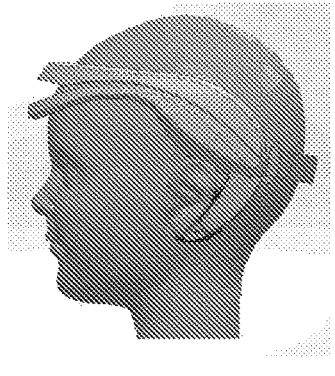
Figure 10E:
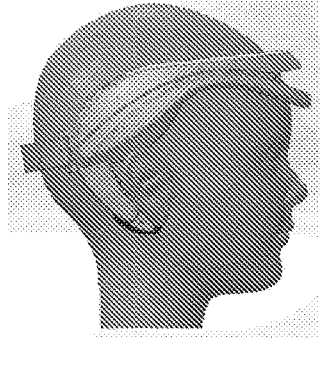
Figure 10F:
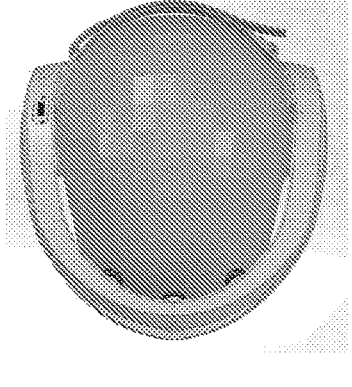
Figure 11A:
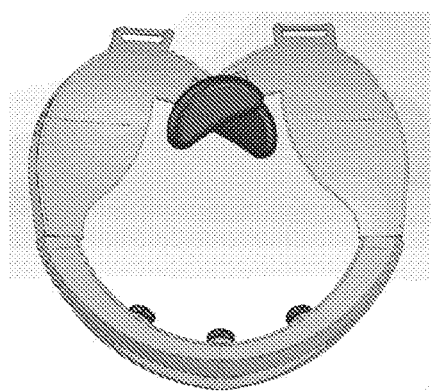
FIGS. 11A-11C depict a headset of the invention having side portions in a folded configuration (i.e., side portions rotated to reduce the size of the headset when not in use).
Figure 11B:
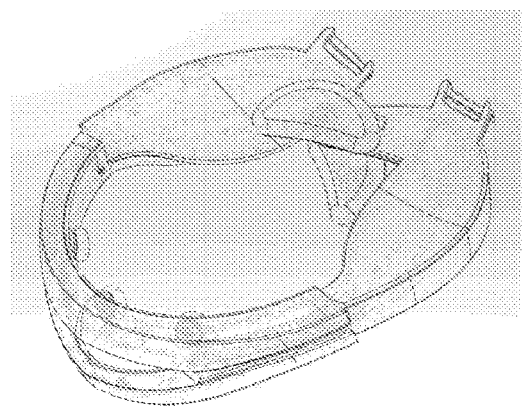
Figure 11C:
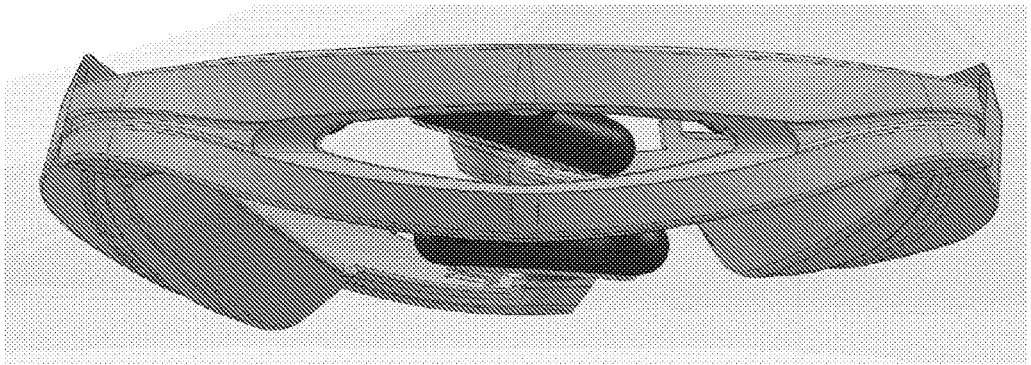
Figure 12A:
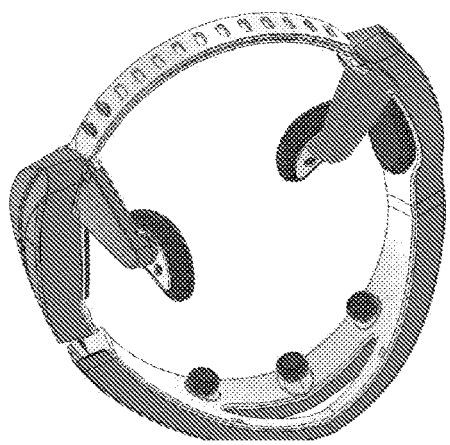
FIGS. 12A-12C depict a headset of the invention having one (FIGS. 12A and 12B) or both (FIG. 12C) mastoid protrusions in a folded configuration (e.g., as a result of a spring force).
Figure 12B:
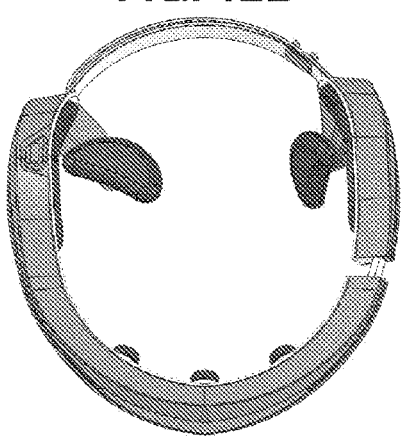
Figure 12C:
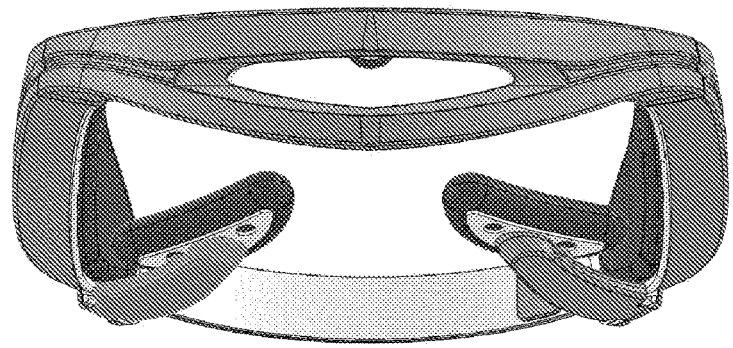
Figure 13A:
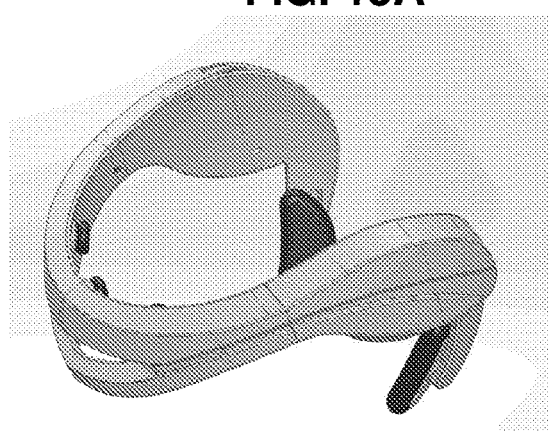
FIGS. 13A and 13B depict a headset of the invention in a non-extended (FIG. 13A) and extended (FIG. 13B) configurations.
Figure 13B:
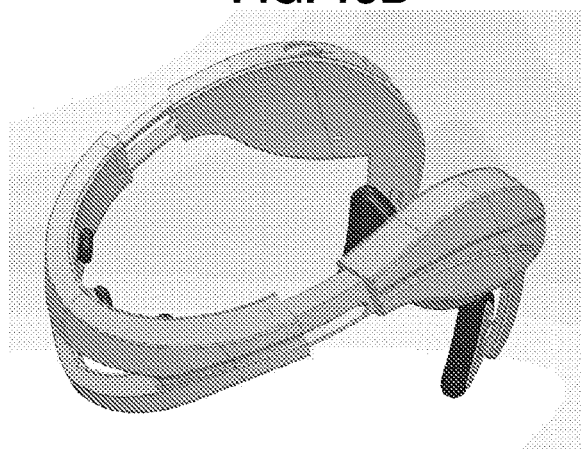

The headsets of the invention contain electrical sensors that measure EEG signals that are processed by an external computer. FIGS. 1-9 depict embodiments of the head sets of the invention.

The electrical sensors can include one or more electrodes for measuring EEG signals of a user. The electrodes can be dry electrodes or wet electrodes (i.e., a dry electrode can obtain a signal without a conductive and typically wet material between the electrode and the user's skin, and a wet material does require such a conductive material). In particular embodiments the electrical sensor includes a dry electrode, such as a dry fabric electrode. Fabric electrodes suitable for use in the headsets of the invention include those described in U.S. Patent Pub. No. 20090112077, incorporated herein by reference. In other embodiments the dry electrical sensor includes a silver electrode. The fabric electrode can include fabric that contains silver, that can be present as silver particles, silver plated strands, or silver thread. In one embodiment the one or more electrical sensors in the sensing bar are circular in shape and about ½ inch (12.7 mm) in diameter. The electrical sensors can contain padding to aid in the comfort of the user and also aid in adjustability and improving skin contact.

The front portion connecting the side portions of the headset includes an upper sensing bar and a lower locator bar. In one embodiment, the inner distance between the sensing bar and the locator bar is approximately 18 mm, and the outer distance from the top of the sensing bar and the bottom of the locator bar is 42 mm. In one embodiment, the front portion is about 119 mm across. In one embodiment, the sensing bar of the front portion contains the electrical sensors that consist of one or more electrodes. In one embodiment the electrical sensors are 7±1 cm apart from center to center. In one embodiment these electrical sensors can be in the form of modules that can snap into place. These modules can potentially be replaced by the user. The electrical sensors can be replaced individually, or there can be a snap in portion that includes more than one electrical sensor. The snap in portion can potentially have sensors that are different widths apart. For example, one snap in portion can have electrical sensors that are 7 cm from center to center, and another snap in portion can have electrical sensors that are 11 cm from center to center. The position of the electrical sensors in the front portion are preferably situated to be over the AF3, AF4, and (optionally) AFz locations on the forehead. In one embodiment, the voltage difference is measured between the AF3 and AF4 electrical sensors. In one embodiment, the electrical sensor at the AFz position is used as a driven ground electrode. In one embodiment, the locator bar of the front portion is designed to stabilize the headset and enable proper positioning of the headset on the forehead. In one embodiment the locator bar has a slight crease in the center that aids the user in centering the headset on his or her forehead.

One or more side portions can also have an electrical sensor. These one or more electrical sensors are preferably located such that the electrodes of the electrical sensor contact the skin of the mastoid process, preferably at positions M1 and M2. This can be accomplished by locating an electrical sensor in a protrusion that extends below the far end of the side portion. In one embodiment at least one of the electrical sensors at positions M1 and M2 are live. In another embodiment on the electrical sensor at the M2 position is live, as to reduce the interfering electrocardiogram signals that can be more prominent at the M1 position. The dimensions of this mastoid electrical sensor can be, for example, two inches long, one inch wide and ¼ inch thick. The electrical sensor can be in a semicircle shape in order to fit behind the ear of the user. The electrical sensor can include padding of foam or another soft material to increase the comfort of the user when wearing the headset. The electrical sensor can be attached to the side portion protrusion by a suspension system that allows the electrical sensors to toe-in and allow for a slight pivot in order to conform to the user when donning the headset. The user may feel a light pressure from the headset when using that assures a good connection between the electrical sensor and the mastoid. In one embodiment an electrical sensor is located such that it contacts the mastoid process at position M2, enabling an measurement of the voltage difference between AF4 and M2. One embodiment of the headset continuously measures the combined impedance of sensing pairs in the difference calculations (AF3-AF4) and (AF4-M2). In one embodiment, an indication of the results of impedance calculations can be sent regularly to the host computer, enabling confirmation that the headset is properly situated for EEG and any attention related measurements.

The electrode systems and headsets of the invention can include electrical sensors having two or more electrodes and configured to contact the forehead of a user at a predetermined position (e.g., AF3, AF4, or AFz). Such a system allows for the selection from among the two or more electrodes (i) the electrode positioned highest on the forehead of a user capable of making a connection with one of positions AF3 or AF4; (ii) the electrode providing the best signal quality; or (iii) the electrode providing the best contact. Such a system is tolerant of a misplacement of the electrical sensors by the user. In one scenario the electrical sensor is positioned by the user such that the upper electrode is in the user's hair and the lower electrode is positioned just below the scalp. In this case, the lower electrode would provide the best connection with AF3 or AF4. In another scenario the electrical sensor is positioned by the user such that the upper electrode is high on the user's forehead, but below the hairline, and the lower electrode is positioned just above the eye brow. In this case, the upper electrode would provide the best connection with AF3 or AF4. A variety of techniques may be used for selecting the appropriate electrode in the electrical sensor. For example, before the headset is placed on the user's head the on-board processor can be configured to test the connections of the electrodes to each other. After the headset is placed on the head of the user the processor can again test the connections of the electrodes to each other by measuring the impedance between the connections. The selection from among the two or more electrodes at an electrical sensor can be performed independently for each electrical sensor in the electrode system or headset. If, for a given electrical sensor, a connection between two electrodes within the sensor is observed, then the processor can be programmed to select the upper electrode (i.e., as the lower electrode is predicted to be too low on the user's forehead to provide a connection with AF3 or AF4). If, for a given electrical sensor, no connection between two electrodes within the sensor is observed, then the processor can be programmed to select the lower electrode (i.e., as the upper electrode is predicted to be positioned above the user's hair line and not providing a quality connection with AF3 or AF4). Alternatively the processor can be configured to be continually measuring the electrical impedance through each electrode to the next one. In this approach the electrode with the lowest impedance is preferentially selected to provide the best contact. Optionally, the processor is configured to monitor the signal to noise ratio from each of the two or more electrodes and, for each electrical sensor, select the electrode having the best ratio (i.e., the least noise) to provide the best signal quality.

The headset of the invention can measure EEG signals. In one embodiment of the headset, the EEG signals can be acquired between 0.25 Hz and 47 Hz −3 dB points relative to 10 Hz. The headset can be designed to acquire EEG signals 0.475 uV resolution (±4.0%) at 10 Hz. The headset can present EEG signals at sample rate of 128 samples/second (±0.05%) and a voltage range of ±1000 µV (±5.0%). The wireless transmission can be via a Bluetooth Low Energy (BTLE) two way connection to a host computer. Lost EEG signal transmissions will be treated as consistent with constraints of BTLE protocols. The headset can initiate EEG acquisition upon wireless request from the host computer with minimal user interaction with the headset after BTLE pairing. The headsets of the invention can be incorporated into a system including an external processor, such an analog or digital signal processor, a co-processing device, and associated memory for storing a series of instructions, otherwise known as a computer program or a computer control logic, to cause the processing system to perform desired functional steps. The headset can be connected to the external processor, for example, via a wireless transmission device. The memory can include a series of instructions defining at least one algorithm for detecting and classifying a predetermined type of mental state, such as an attentive or inattentive mental state. Upon detection of a predefined mental state, a corresponding control signal is transmitted to an input/output interface. From the input/output interface, the control sign can be transmitted to a platform for use as a control input by a gaming application, program, simulator, or other application.

The systems of the invention include a headset in communication (e.g., a wireless connection) with an external processor equipped with a computer program capable of, for example, processing the EEG signal to determine the attention state of the user, in a system with several electrical sensors with integrated electrodes that acquire EEG signals, and/or providing feed-back to the user in the form of a game. The computer program can be housed in many different types of computers such as a desktop computer, laptop computer, tablet, gaming system, or cellular phone. As part of a game, the system can be configured to operate, for example, as described in U.S. Patent Pub. No. 20120108997, incorporated herein by reference. Methods for processing the EEG signal to determine the attention state of the user are described, for example, in U.S. Pat. No. 8,862,581, U.S. Patent Pub. No. 20130331727, and PCT Pub. No. WO2013147707 A1, each of which is incorporated herein by reference.

An embodiment of the headset of the invention includes a battery. The battery is commonly a lithium ion battery. The battery can have sufficient battery capacity with ≥98% state of health (SOH) to support communication of EEG signal to a host computer for ≥4 hours. The headset can charge the battery sufficiently for ½ hour of use in <¼ hour (≥98% SOH). The battery can be rechargeable by an external power supply. In one embodiment, the external power supply is located in a computer. In one embodiment, the battery shall be rechargeable in <4 hours, from 10% to 90% state of charge (SOC) for a battery with ≥98% SOH, subject to the safety requirements of the battery. In one embodiment the battery state of charge is reported to a host computer. The state of battery charge may also be reported to a user. In one embodiment, the battery shall be specified to accommodate >300 charge-discharge cycles without losing more than 50% SOH. In one embodiment, storage of the headset with the included battery between 0° C. and 20° C. for ≥1 year with recoverable battery capacity with no more than a 20% reduction in SOH of the initial battery capacity, or as consistent with selected and accepted battery specifications is enabled. In one embodiment, storage between 0° C. and 43° C. for ≥3 months with recoverable battery capacity no more than a 20% reduction in SOH of the initial battery capacity, or as consistent with selected and accepted battery specifications is enabled. In one embodiment, the battery can be optionally replaceable by the user. In one embodiment, the battery specifications and charge or SOC requirements are commensurate with the two year minimum life cycle. In one embodiment, the headset is charged through a USB connection. That connection can be used to connect to a host computer, docking station, or other AC power adapter to charge the battery of the headset. In one embodiment, the battery switches to a deep sleep mode if it has not connected wirelessly or through a wired connection in over 30 days.

An embodiment of the headset includes software. In another aspect, the software can include firmware. Preferably, the firmware is upgradable without disassembly of the headset. In one embodiment the software is protected from reading by unauthorized people or entities. The software can be encrypted or not encrypted.

The headset is ideally worn by an 8-17 year-old child with minimal instruction. The headset preferably should be worn properly by the child within the first three attempts following instructions for use. The headset is designed to be comfortable by minimizing the weight and pressure on the head of the user.

One embodiment of the headset includes a strap that connects the two side portions. The strap can include a tightening mechanism that encourages adjustability. The strap can be of a molded material. The strap can include an adjustment mechanism that includes a closure with a post and hole or a medical grade hook and loop. The strap can also be made of a more flexible material including woven fabric or silicone that also adjustable.

Other embodiments of the headset include elements that enable adjustability of the headset, e.g., to promote optimal fit on a user's head or for ease of storage. The side portions of the headset can be slidably coupled to the front portion to allow extension of the side portions and/or mastoid protrusions from front to back. Additionally or alternatively, the side portions can be rotatably coupled to the front portion, e.g., to accommodate various head shapes or to allow for folding for easy storage. The headset can additionally, or alternatively, feature one or more hinged mastoid protrusions. Hinged mastoid protrusions enable, for example, a user to fold the protrusions up for easy storage. In some embodiments, hinges promote contact of the mastoid electrode to the user's head, for example, by an inward force exerted by a spring mechanism within the hinge.

One embodiment of the headset includes an accelerometer. The inclusion of the accelerometer will allow for the translation of head movements into video game application mechanics and movements (e.g., the user can cause a game avatar to jump by moving the user's head upward). An accelerometer could also serve as a quantifier for activity in the user and potentially be useful as a diagnostic for activity disorders.

Another embodiment includes a location identifier. This could be radio frequency identification, global positioning system, or other microchip to enable the finding of the headset. This locating feature provides a means for locating a headset that has been misplaced by the user. The location identifier can allow the finding of the headset if it is within 50 meters of the host computer, and make an audible noise that will alert the user to its location. The headset can respond to wireless request for location identifier sound from host within 10.3 seconds, except when the headset is in use. The location identifier sound is preferably at least 50 dB at 1 meter and is audible within 50 meters of the host computer. In one embodiment the headset can be located using the wireless locating device for 6 days after a full battery charge (100% SOC, ≥98% SOH) and 1.5 hours of use. In one embodiment, the headset activates a finder feature to regularly reestablish a connection to a host computer. If the headset has been unable to establish a connection to a host computer in 30 days, it can trigger a deep sleep mode to preserve battery function. Once in deep sleep mode, the headset must be charged at the host computer in order to reestablish the activity of the headset.

One embodiment of the headset includes a unique device identifier. This can include a media access control address (MAC address). It can also include a serial number.

LED elements present in the headset can be lit in response to the attention state of the user or, when part of a gaming system, in response to events occurring in the game and/or the user's game performance. LEDs can also indicate the charging state of the battery. In one embodiment an LED on the headset is amber when charging and green when charged.

In one embodiment, the EEG signals obtained from the electrical sensors at the AF3 and AF4 positions derive from the cingulate anterior cortex of the user. It is theorized that the dorsal anterior cingulate cortex becomes active in children who exhibit attention deficit hyperactivity disorder (ADHD). Thus, monitoring the brain signals obtained from that region should be informative when children with ADHD use the headset.

OTHER EMBODIMENTS

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A headset comprising:
   (i) a front portion comprising a first end, a second end, a sensing bar, and a locator bar, wherein the sensing bar and the locator bar are joined at the first end and the second end of the front portion and comprising a space below the sensing bar and above the locator bar between the first end and the second end, and wherein:
   (a) the sensing bar is shaped and configured to contact the forehead of a user wearing the headset and comprises a first electrical sensor positioned to contact the forehead of the user at about position AF3, the first electrical sensor comprising one or more electrodes, and a second electrical sensor positioned to contact the forehead of the user at about position AF4, the second electrical sensor comprising one or more electrodes, and
   (b) the locator bar is shaped and configured to rest upon the brow of the user to aid the user in positioning the first electrical sensor at about position AF3 and position the second electrical sensor at about position AF4; and
   (ii) a first side portion and a second side portion, the first side portion joined to the first end of the front portion and the second side portion joined to the second end of the front portion, wherein the first side portion, the second side portion, and the front portion, together, are shaped and configured to grip the head of the user, and wherein the first side portion is rotatably coupled to the first end of the front portion and the second side portion is rotatably coupled to the second end of the front portion to permit the first side portion and the second side portion to fold inward and reduce the size of the headset when not in use.

2. The headset of claim 1, and wherein at least one of the first side portion and the second side portion further comprise a protrusion, the protrusion comprising a third electrical sensor positioned to contact the user at about position M2 or M1, the third electrical sensor comprising one or more electrodes that contact the skin over the mastoid process of the user.

3. The headset of claim 2, further comprising a processor equipped with an electronics for selecting and detecting a difference in voltage between (i) AF3 and AF4, and (ii) AF4 and M2 or AF3 and M1.

4. The headset of claim 1, wherein the first side portion and the second side portion are shaped and positioned to contact the skin over the temporal bone of the user.

5. The headset of claim 4, wherein the headset is shaped to permit the user to wear the headset and eyeglasses simultaneously.

6. The headset of claim 1, wherein the maximum distance between the inside edge of the locator bar and the inside edge of the sensing bar is 15±2 mm, 18±2 mm, or 20±2 mm.

7. The headset of claim 1, wherein the maximum distance between the outside of the locator bar and the outside of the sensing bar is 40±2 mm, 42±2 mm, or 44±2 mm.

8. The headset of claim 1, wherein each of the first side portion and the second side portion further comprise padding positioned to contact the head of the user.

9. The headset of claim 8, wherein at least one of the first electrical sensor, the second electrical sensor, and the third electrical sensor is ½ inch or greater in at least one dimension.

10. The headset of claim 8, wherein at least one of the first electrical sensor, the second electrical sensor, and the third electrical sensor further comprises padding positioned to contact the skin of the user.

11. The headset of claim 1, wherein at least one of the first electrical sensor, the second electrical sensor, and the third electrical sensor comprise a dry electrode.

12. The headset of claim 1, wherein at least one of the first electrical sensor, the second electrical sensor, and the third electrical sensor comprise a fabric electrode.

13. The headset of claim 1, wherein at least one of the first electrical sensor, the second electrical sensor, and the third electrical sensor comprise a silver electrode.

14. The headset of claim 1, wherein at least one of the first electrical sensor, the second electrical sensor, and the third electrical sensor comprise a silver fabric electrode.

15. The headset of claim 14, wherein the first electrical sensor and the second electrical sensor comprise a silver fabric electrode.

16. The headset of claim 1, wherein the sensing bar comprises sockets for directly securing the first electrical sensor and the second electrical sensor, or for receiving a mounting element into which the first electrical sensor and the second electrical sensor are secured.

17. The headset of claim 16, wherein the mounting element is adjustable to permit control over the spacing between the first electrical sensor and the second electrical sensor.

18. The headset of claim 16, wherein the first electrical sensor and the second electrical sensor are spaced 7±1 cm apart from center to center.

19. The headset of claim 16, wherein the first electrical sensor and the second electrical sensor are spaced from 8 cm to 10 cm apart from center to center.

20. The headset of claim 1, wherein the locator bar has a slight crease at the center of the locator bar.

* * * * *